United States Patent [19]

Stansfeld et al.

[11] Patent Number: 4,962,671
[45] Date of Patent: Oct. 16, 1990

[54] SINGLE VIBRATING TUBE TRANSDUCERS

[75] Inventors: James W. Stansfeld, Nr. Alton; David I. H. Atkinson, Farnham, both of England

[73] Assignee: Schlumberger Industries Limited, Farnborough, England

[21] Appl. No.: 273,452

[22] Filed: Nov. 18, 1988

[30] Foreign Application Priority Data

Nov. 19, 1987 [GB] United Kingdom ............... 8727100

[51] Int. Cl.$^5$ .................................................. G01F 1/84
[52] U.S. Cl. .................................. 73/861.37; 73/32 A
[58] Field of Search .............. 73/32 A, 861.37, 861.38

[56]  References Cited
U.S. PATENT DOCUMENTS 3,585,843  6/1971  Stansfeld ........................... 73/32 A
4,760,744  8/1988  Simonsen et al. ................ 73/861.38
4,823,614  4/1989  Dahlin ................................ 73/861.38

Primary Examiner—Herbert Goldstein
Attorney, Agent, or Firm—Sanford J. Asman

[57] ABSTRACT

A single vibrating tube transducer comprises a tube (4) held between two nodal masses (6) which are attached to the tube (2) close to their respective centers of gravity (16). Each nodel mass (6) has an extended portion (14) which is attached at its free end to the opposing nodal mass by an arrangement of metal ligaments (18). Vibrating means (19) and sensing means (20) drive and detect the tube motion respectively. The tube has discontinuities (28) adjacent to the vibrating means (19) and the sensing means (20), to ensure the desired mode of resonance is achieved. Acoustic baffles (30) prevent inaccuracies due to internal acoustic resonance in the transducer.

14 Claims, 2 Drawing Sheets

SINGLE VIBRATING TUBE TRANSDUCERS

BACKGROUND OF THE INVENTION

This invention relates to single vibrating tube transducers which are typically used to measure mass, density, or mass flow.

Transducers of this kind are very well known. One example is described in our patent specification GB No. 2 062 865. Such transducers exploit the well known fact that fluid flowing in a vibrating tube which is clamped at its two ends will produce a phase difference between the transverse displacements of the upstream and downstream ends of the tube. The mass flow rate of a fluid in such a tube is a linear function of the ratio A of the phase difference to the resonant frequency of the tube, where $$A = \phi/F$$

$\phi$ being the phase difference and F being the resonant frequency of the tube. The mass flow rate M is then give by $$M = aA + b$$

where a and b are constants and are independent of the fluid type and flow rate.

Transducers of this type are subject to variations in accuracy due to external vibrations and shocks when they are used in hazardous environments. Problems have also been encountered due to the vibrating tube setting up an acoustic resonance between the tube and the instrument casing. Another problem is the fact that antinodes of vibration may be set up at points on the tube distant from the means for sensing the vibrations and will thus cause inaccuracies in phase difference measurement.

Known measures (GB No. 2 062 865) for overcoming some of these problems include slight ellipticity of the tube to define the vibrational mode; this imposes manufacturing problems. The nodes are typically clamped by nodal masses and in GB No. 2 062 865 these masses are extended towards each other around the vibrating tube and connected by a flexible bellows to form a sealed enclosure which can be evacuated to present contamination of the components by dust etc. which may cause inaccuracies. Maintenance of an evacuated enclosure imposes problems in use. Moreover the extended nodal masses have a centre of gravity displaced from the nodal point of attachment to the tube and shocks can be communicated to the tube too easily.

The object of the present invention is to provide more satisfactory solutions to the problems dealt with above.

The present invention is defined in the appended claims to which reference should now be made.

DETAILED DESCRIPTION OF AN EXEMPLARY EMBODIMENT

Figure 1:
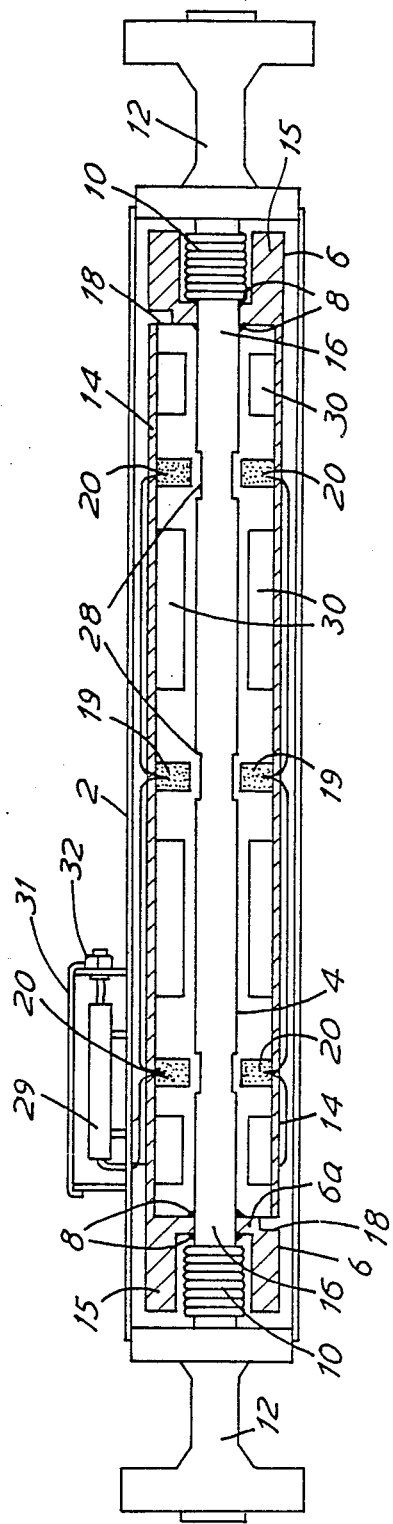
FIG. 1 is a longitudinal cross-section through a transducer embodying the invention.

The transducer shown in FIG. 1 is protected from damage by a cylindrical casing 2. Mounted centrally in the casing 2 is a generally cylindrical tube 4 through which the fluid to be measured passes. Each end of the tube 4 passes through a nodal mass 6 and is rigidly attached thereto by two circumferential welds 8, one on either axial side of an inner annular portion 6a of the nodal mass closely fitting on the tube 4.

The ends of the tube 4 are connected to cylindrical bellows 10 which absorb the thermal expansion of the tube and the external pipes, and also protect the tube from noise and vibration in the external pipes. The bellows are connected to flange pieces 12 which seal the ends of the casing 2 and also provide means to connect the transducer into a main line.

The two nodal masses 6 have arcuate extended portions 14 which run substantially the length of the tube 2, preferably on opposing sides of the tube. These are welded to the inner annular portion 6a once it has been welded to the tube. A typical cross-section through one of these extended portions 14 can be seen in FIG. 2. Each nodal mass has its weight distributed in such a way that its centre of gravity 16 is on the axis of the tube 4 and axially between the two welds 8 attaching it to the tube 4.

To this end, each cantilevered extension 4 is counterbalanced by a sleeve extension 15 rearwardly cantilevered from the inner annular portion 6a. The extension 15 is welded to the inner annular portion once it has been welded to the tube. This ensures that any movement of the instrument due to plant vibration or shock will not impose excessive stresses in the vibrating tube, which would cause the transducer to give inaccurate readings.

The double weld 8 attaching each nodal mass 6 to the tube 4 helps to protect the tube 4 against transverse shocks by reducing the tendency of the nodal mass to pivot when the transducer is subjected to transverse shocks. The fact that the nodal masses are in three or more sections enables this double weld to be made relatively easily since the inner annular portions 6a can be easily accessed before the cantilevered sections 14 and 15 are welded on.

Figure 2:
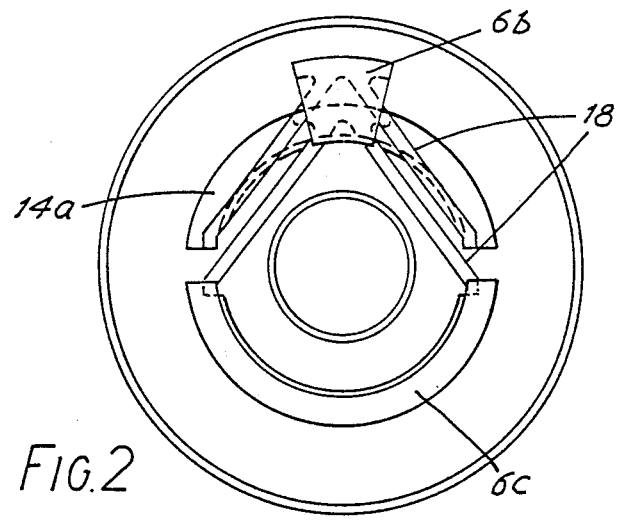
FIG. 2 is an axial view of a connection between the two nodal masses in this embodiment of the invention.
Figure 3:
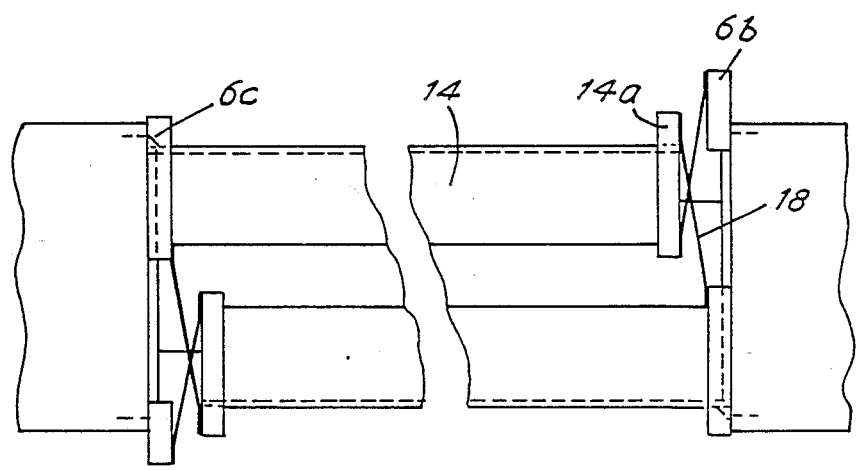
FIG. 3 is a side view of the connections between the two nodal masses in this embodiment of the invention.

The end of the extended portion 14 of each nodal mass is linked to the opposing nodal mass by an arrangement of thin metal strip ligaments 18, as illustrated in FIG. 2 and FIG. 3. In this embodiment, four ligaments 18 are used and are so arranged that at least one of them is always in tension when the transducer is subject to transverse shocks and vibrations, i.e., the link arrangement is rigid transversely. The links do however allow for axial movement of the nodal masses. This linking together of the nodal masses substantially increases their inertial mass which helps to keep the ends of the tube stationary when the tube is vibrating.

In order to ensure that at least one link 18 is always in tension, they are arranged in two crossing pairs but the points of attachment of their ends are transversely offset in such a way that the links do not touch where they cross. In the arrangement of FIGS. 2 and 3, the nodal masses each have a transversely extending first arcuate section 6b fixed to the inner annular section 6a and a second arcuate section 6c fixed between the inner annular section and the extended portion 14 on the opposite side of the tube to the first arcuate section 6b. The extended portion 14 has a third arcuate section 14a at its distal end. A first pair of ligaments is welded at one end to the first arcuate section 6b and at the other end each is welded to opposite ends of the third arcuate section 14a. A second pair of ligaments extends from the centre of the third arcuate section 14a to opposite ends of the second arcuate section 6c. Thus the two pairs of ligaments are transversely offset and do not touch when they cross and whatever the relative movement of the two nodal masses, at least one ligament will always be in tension.

To ensure that one ligament 18 is always in tension a minimum of two are required, but the arrangement described here with four ligaments is more rigid.

Mounted on the extended portions 14 of the two nodal masses are the vibrating means 19 to drive the tube at a central anti-node and the sensing means 20 at further anti-nodes on the tube to detect the vibrations of the tube. In the embodiment shown here the vibrating means and sensing means are in pairs on either side of the tube, one from each pair being fixed to each nodal mass.

Figure 4:
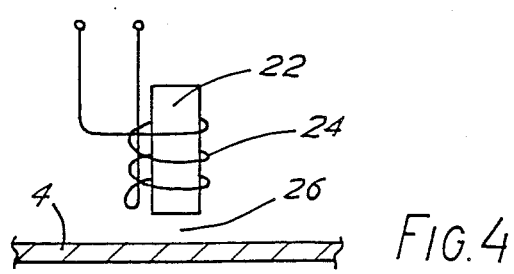
FIG. 4 illustrates a preferred embodiment of the drive means for vibrating the tube.

The vibrating means and the sensing means for this embodiment are shown in FIG. 4. They comprise a permanent magnet 22 with its axis perpendicular to the wall of the tube. An electric coil 24 is wound round the magnet. The magnet has a small gap 26 of around 0.1 mm between it and the tube which is made from a magnetic material. An alternating voltage is applied to the coil which produces an alternating magnetic field in the gap 26 which causes the magnetic tube to vibrate at the frequency of the alternating voltage. With a drive means on either side of the tube as is the case with this embodiment, the polarities of the two coils are reversed so thay they are both moving the tube in the same direction at the same time.

The same device can be used for the sensing means. The natural resonant vibration of the magnetic tube in the gap 26 produces an a.c. voltage on the coil 24. The frequency of this a.c. voltage is equal to the frequency of vibration of the tube. The vibrations are self sustaining having been triggered by s small purturbation. They are sustained by a positive feedback loop between the pick-up coils and the drive coils. When the transducer is used to measure density, only one set of pick-up coils is required to measure the frequency of vibration.

The vibrating means and the sensing means are controlled by a control circuit 28 located within an external housing 30. This has a power input/signal output connection 32. For mass flow measurements, the control circuit evaluates the phase difference between the two sensing means locations on the tube in a manner similar to that described in our British patent application no. 86 17415.

In the embodiment shown here the vibrating weans is mounted equidistantly from the two nodal masses and the two sensing means are located symmetrically about the vibrating means.

The vibrating means 19 is located at an anti-node halfway between the two nodal masses. In this embodiment there are two further anti-nodes between each nodal mass 6 and the vibrating means 19.

Adjacent to each vibrating means and each sensing means, material has been removed to produce a localised flat surface 28. These flat surfaces, which reduce the tube stiffness at that point, ensure a mode of vibration with these positions as anti-nodes. These flats 28 also improve the performance of the vibrating means and sensing means since the gap 26 between the flat end of each magnet pole piece and the tube is now parallel.

Other discontinuities could be introduced to the tube at these locations to ensure that they become anti-nodes, and this may involve the addition instead of the removal of material.

Also attached to the extended portions 14 of the nodal masses are acoustic baffles 30. These baffles 30 are between the tube and the nodal masses but do not contact the tube. The purpose of these baffles is to prevent any acoustic resonance within the transducer casing without having to evacuate the tube of gas. This resonance would affect the vibration of the tube and cause inaccuracies in measurement. The baffles are typically made from a foamed plastics material or a honeycomb composite material. This type of material has good acoustic absorption properties because of the voids in its structure.

The improvements described above are intended to be applied to any type of vibrating tube transducer. The improvements provide a transducer which is much less susceptible to external shocks and vibrations, which has its resonant mode better defined, and which is not subject to inaccuracy due to internal acoustic resonance.

The transducer described here is one embodiment of the invention and variations in this are possible. For example, the extended portions of the nodal masses need not be arcuate and could in fact have any cross-section. A rectangular cross-section would be advantageous in increasing the stiffness thereof. If used with the density transducer of our GB No. 2 062 865 they might be elliptical for use with an elliptical tube. The linkages between nodal masses could have a larger number of ligaments in order to add rigidity.

We claim:

1. A single vibrating tube transducer comprising a straight tube through which a fluid to be measured flows, first and second nodal masses attached to respective ends of the tube, means for vibrating the tube, and at least one means for sensing the vibrations of the tube, wherein each nodal mass has a first extended portion extending alongside the tube towards the other nodal mass and a second oppositely extending portion counterbalancing the first portion and rendering the centre of gravity proximal to the point of attachment of the mass to the tube.

2. A transducer according to claim 1, wherein each first extended portion extends substantially the length of the tube, the two extended portions being on opposed sides of the tube and each extended portion being linked to the opposing nodal mass close to the point of attachment of the said opposing nodal mass to the tube.

3. A transducer according to claim 2, wherein the linkages between the opposing nodal masses are substantially rigid transverse to the axis of the tube, and at least partially flexible axially of the tube.

4. A transducer according to claim 2, wherein each linkage between the opposing nodal masses comprises at least two thin metal strips extending in directions such that at least one strip is always in tension.

5. A transducer according to claim 1, wherein each nodal mass comprises an annular portion fitting on the tube and rigidly fixed to the tube on both axial sides of the annular portion.

6. A single vibrating tube transducer comprising a straight tube through which a fluid to be measured flows, means for vibrating the tube, at least one means for sensing the vibrations of the tube and first and second nodal masses attached to respective ends of the tube, wherein each nodal mass extends substantially the length of the tube, the two extended portions being on opposing sides of the tube, and each extended portion being linked to the opposing nodal mass close to the point of attachment of the said opposing nodal mass.

7. A transducer according to claim 6, wherein the linkages between the opposing nodal masses are substantially rigid transverse to the axis of the tube and at least partially flexible axially of the tube.

8. A transducer according to claim 6, wherein each linkage between opposing nodal masses comprises at least two thin metal strips extending in directions such that at least one strip is always in tension.

9. A single vibrating tube transducer comprising a straight tube through which a fluid to be measured flows, means for vibrating the tube, at least one means for sensing vibrations of the tube and first and second nodal masses attached to respective ends of the tube, wherein the tube is shrouded within extended portions of the nodal masses, which create an annular gap between the extended portions and the tube, and wherein at least one acoustic baffle is inserted within said gap.

10. A transducer according to claim 9, wherein the baffle(s) are attached to the insides of the extended portions.

11. A single vibrating tube transducer comprising a straight tube through which a fluid to be measured flows, means for vibrating the tube, at least one means for sensing the vibrations of the tube wherein the tube is of uniform circular section except for at least one flat which is machined on its external surface at at least one desired anti-node on the tube.

12. A transducer according to claim 11, wherein diametrically-opposed flats are machined on the external surface of the tube at the or each desired anti-node.

13. A transducer according to claim 11, wherein flats are machined on the external surface of the tube at at least three desired anti-nodes, and the vibrating means and a first and a second sensing means are positioned adjacent to respective anti-nodes.

14. A transducer according to claim 13, wherein each vibrating or sensing means comprises an electromagnetic device with a flat pole piece spaced closely parallel to the respective flat on the tube.

* * * * *